(12) United States Patent
Bi

(10) Patent No.: US 8,850,874 B1
(45) Date of Patent: Oct. 7, 2014

(54) IN-LINE VISCOMETER

(76) Inventor: Hongfeng Bi, Houston, TX (US)

( * ) Notice: Subject to any disclaimer, the term of this patent is extended or adjusted under 35 U.S.C. 154(b) by 368 days.

(21) Appl. No.: 13/343,902

(22) Filed: Jan. 5, 2012

(51) Int. Cl.
G01N 11/14 (2006.01)
(52) U.S. Cl.
USPC .......................................................... 73/54.28
(58) Field of Classification Search
CPC .................. G01N 11/14; G01N 2011/147
USPC ............................... 73/54.28–54.35
See application file for complete search history.

(56) References Cited

U.S. PATENT DOCUMENTS

| | | | | | |
|---|---|---|---|---|---|
| 2,237,743 | A | * | 4/1941 | McIntyre ..................... | 73/54.31 |
| 2,485,424 | A | * | 10/1949 | Weisz ......................... | 73/54.31 |
| 2,679,157 | A | * | 5/1954 | Carpenter ................... | 73/54.31 |
| 3,751,975 | A | | 8/1973 | Katsura | |
| 4,524,611 | A | | 6/1985 | Richon et al. | |
| 4,557,142 | A | * | 12/1985 | Hensley et al. ............ | 73/152.19 |
| 4,643,021 | A | | 2/1987 | Mattout | |
| 4,765,180 | A | * | 8/1988 | Clifton ........................ | 73/54.33 |
| 5,606,115 | A | | 2/1997 | Kamrat | |
| 5,694,341 | A | * | 12/1997 | Song, II ...................... | 702/173 |
| 5,798,454 | A | | 8/1998 | Nakazeki et al. | |
| 6,145,373 | A | * | 11/2000 | Tymchuck ................... | 73/54.28 |
| 6,167,752 | B1 | * | 1/2001 | Raffer .......................... | 73/54.28 |
| 6,257,051 | B1 | * | 7/2001 | Boyle et al. ................. | 73/54.01 |
| 6,412,338 | B2 | | 7/2002 | Boyle et al. | |
| 6,499,336 | B1 | * | 12/2002 | Raffer ......................... | 73/54.28 |
| 6,640,617 | B2 | | 11/2003 | Schöb et al. | |
| 6,691,559 | B2 | | 2/2004 | Robinson | |
| 6,691,560 | B2 | | 2/2004 | Abnett | |
| 7,287,416 | B1 | * | 10/2007 | Bi ................................ | 73/54.28 |
| 7,412,877 | B1 | * | 8/2008 | Bi ................................ | 73/54.28 |
| 7,549,324 | B2 | * | 6/2009 | Haapasaari et al. ......... | 73/61.41 |
| 7,568,380 | B2 | | 8/2009 | Bivens et al. | |
| 8,171,776 | B2 | * | 5/2012 | Andersson et al. .......... | 73/54.28 |
| 8,375,771 | B1 | * | 2/2013 | Bi ................................ | 73/54.33 |
| 2001/0042400 | A1 | * | 11/2001 | Boyle et al. ................. | 73/54.28 |
| 2003/0033859 | A1 | * | 2/2003 | Schoeb et al. ............... | 73/54.28 |
| 2003/0192366 | A1 | * | 10/2003 | Taylor ......................... | 73/54.32 |
| 2007/0193344 | A1 | * | 8/2007 | Haapasaari et al. ......... | 73/61.41 |
| 2010/0116034 | A1 | * | 5/2010 | Abbott et al. ................ | 73/54.35 |
| 2010/0162798 | A1 | * | 7/2010 | Gautsch ....................... | 73/54.28 |
| 2010/0269571 | A1 | * | 10/2010 | Raffer .......................... | 73/54.28 |
| 2012/0210774 | A1 | * | 8/2012 | Raffer .......................... | 73/54.28 |

* cited by examiner

Primary Examiner — John Fitzgerald

(57) ABSTRACT

An in-line viscometer (70) with a coupling magnet (42) installed into a bob (44) and a drive magnet (24) installed onto a magnet holder (52). Coupling magnet (42) forms a magnetic coupling with drive magnet (24). Bob (44) is positioned inside a main body (50) and is submerged in the flow of sample fluid (56). A motor (10) rotates a magnet holder (52) to which the drive magnets (24) are attached. The magnetic coupling between the coupling magnet (42) and the drive magnet (24) causes the bob (44) to rotate while submerged in sample fluid (56). The energy necessary for the motor (10) to turn the magnet holder (52) while the bob (44) is submerged in the sample fluid (56) provides a means to measure the viscosity of the sample fluid (56).

20 Claims, 3 Drawing Sheets

IN-LINE VISCOMETER

BACKGROUND

1. Field of Invention

The present invention relates to a viscometer which measures the viscosity of a fluid by rotating a bob within the fluid, the viscosity of which is to be determined. Measurement of the energy necessary to rotate the bob within the fluid is used to determine the viscosity of the fluid. This invention could be used in a conduit such as pipe or manifold to measure the fluid within the working environment of the fluid or it could be operated in a laboratory environment.

2. Description of Prior Art

The measurement of the viscosity of a fluid flowing in a pipe or other conduit is well known but can be problematic. Particularly difficult fluids to measure are fracturing fluids and gels used in fracturing of well formations. The viscosity of the fluid is, of course, measurable before it is pumped into the well, but this measurement is not always satisfactory because the viscosity of the fluid may change in the well. Heat and other well conditions may affect the fluid in ways that are not entirely predictable. Therefore, it is desirable to be able to measure the viscosity of such fluids "on the fly" as the fluid is flowing through the pipe. A viscometer for this purpose is called an "in-line" viscometer.

U.S. Pat. No. 4,524,611 teaches a rheometer comprising a hollow body 2 with an inner shaft 9 which is driven to rotate via a coupling with magnet 12A. Unfortunately, this rheometer could not be used in-line because the magnet 12A would become submerged in sample fluid, which would inevitably create measurement errors due to the fluid flow. Additionally, the position of inner shaft 9 is maintained at top and bottom by a pin and jewel bearing, which are not configured such that they could sustain as much radial directional disturbance as would be present in a pipeline filled with a flowing fluid.

U.S. Pat. No. 7,568,380 teaches a patent for an in-line turbine viscometer. It suspends a turbine within a pipe containing a flowing fluid, and uses magnets as the impetus for the rotation of the turbine. The drawback to this approach is that the flow of the fluid makes it impossible to control or even define a specific shear rate for the turbine rotation. If fluid flow falls below a certain level, measurement becomes riddled with errors or stops entirely.

U.S. Pat. No. 6,640,617 teaches an in-line apparatus and a method for determining the viscosity of a fluid which places an electrical rotary drive having a stator with a stator winding and a rotational body into a pipeline filled with a flowing fluid. The rotational body is suspended and driven to rotate by a magnetic field generated by sets of coils. This apparatus is very complicated and expensive to manufacture due to its sophisticated magnetic field suspension and control.

U.S. Pat. No. 4,643,021 teaches a method of measuring the rheological characteristics of a fluid by magnetically suspending a cylinder immersed in the fluid which is to be tested and rotating said cylinder via magnetic suspension. This apparatus is not, however, suitable for use as an in-line measurement method and further, is complicated and expensive to manufacture due to the nature of magnetic suspension technology.

It is an object of this invention to provide a practical and affordable in-line device for accurately testing the viscosity of a flowing fluid without compromising the integrity or performance of the working environment of the fluid.

It is another object of this invention to provide a viscosity measurement device which uses magnetic force to suspend a bob in the fluid, the viscosity of which is to be determined, and rotate the bob using magnetic coupling, measuring the energy required to rotate the bob and using that measurement to determine the viscosity of the fluid.

It is another object of this invention to provide a viscosity measurement device which requires substantially less maintenance work than other designs yet meets industry standards of accuracy, repeatability, durability, and ease of cleaning

SUMMARY OF THE PRESENT INVENTION

A viscometer in accord with the present invention is comprised of a main body filled with a sample fluid, the viscosity of which is to be determined. Inside the main body is a cylindrical main shaft. A cylindrical bob extends radially outward from the main shaft. A coupling magnet is installed inside the cylindrical bob. A drive magnet is caused to rotate outside of the main body, which causes the coupling magnet and the bob to rotate as well, due to magnetic coupling. The magnetic coupling also causes the bob to be partially suspended within the sample fluid while a pair of jewel bearings restrict the bob to rotational movement only.

In the preferred embodiment, a cylindrical main shaft is positioned between a fluid inlet and a fluid outlet. At the top of the main shaft is a bearing holder attached to a bob containing a coupling magnet. Outside the main body is a magnet holder provided with a drive magnet. The magnet holder is suspended from a motor support and is driven to revolve by a motor affixed to the top of the motor support. Because of a magnetic coupling between the drive magnet and the coupling magnet, the revolving drive magnet causes the bob and the attached coupling magnet to rotate while being submerged in sample fluid. The viscosity of the fluid is determined by measuring the amount of energy necessary to turn the bob via magnetic coupling.

In the second embodiment, a cylindrical main shaft is positioned inside a cell body which is filled with sample fluid. At the bottom of the main shaft is a bearing holder attached to a bob containing a coupling magnet. Outside the main body is a magnet holder provided with a drive magnet. The magnet holder is positioned at the top of a motor support and is driven to revolve by any conventional means such as a gear box or motor. Because of a magnetic coupling between the drive magnet and the coupling magnet, the revolving drive magnet causes the bob and the attached coupling magnet to rotate while being submerged in sample fluid. The viscosity of the fluid is determined by measuring the amount of energy necessary to turn the bob via magnetic coupling.

In the third embodiment, a cylindrical main shaft is positioned between a fluid inlet and a fluid outlet. At the top of the main shaft is a bearing holder attached to a bob containing a coupling magnet. The coupling magnet is positioned near the top of the bob. Outside and above the main body is a magnet holder provided with a drive magnet. The magnet holder is suspended from a motor support and is driven to revolve by a motor affixed to the top of the motor support. Because of a magnetic coupling between the drive magnet and the coupling magnet, the revolving drive magnet causes the bob and the attached coupling magnet to rotate while being submerged in sample fluid. The viscosity of the fluid is determined by measuring the amount of energy necessary to turn the bob via magnetic coupling.

DRAWING FIGURES

Other objects, features and advantages will be apparent from the following detailed descriptions of embodiments taken in conjunction with accompanying drawings in which.

Figure 1:
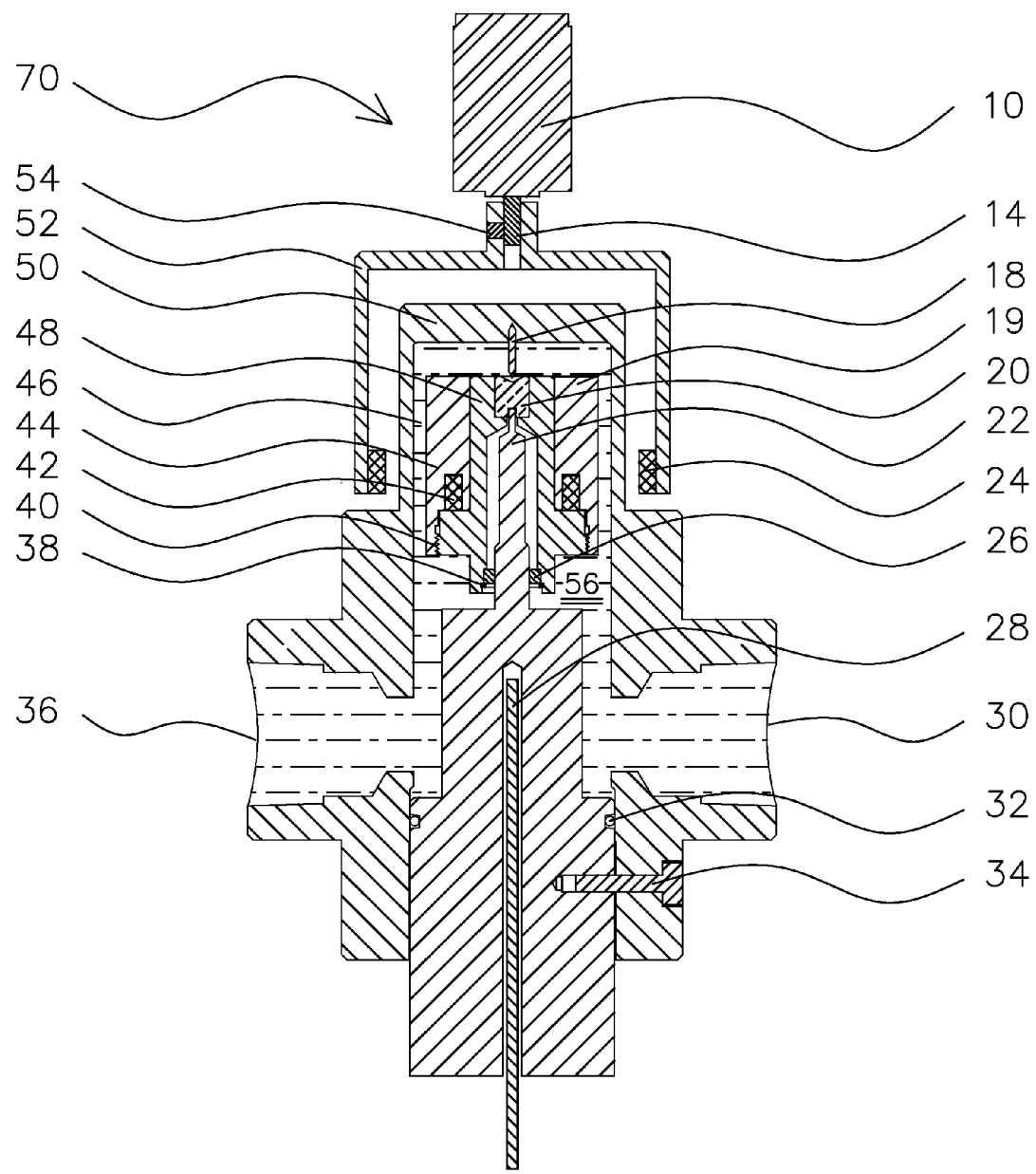
FIG. 1 is a cross-section view of an in-line viscometer 70 in the preferred embodiment of the invention.

| Reference Numerals in Drawings | |
|---|---|
| 10 motor | 10B motor |
| 12A upper external retainer ring | 14 motor shaft |
| 14B motor shaft | 16A bearing |
| 18 pin | 18B pin |
| 19 bob assembly | 19A bob assembly |
| 19B bob assembly | 20 jewel bearing |
| 20B jewel bearing | 22 main shaft |
| 22A bob holder | 22B main shaft |
| 24 drive magnet | 24A drive magnet |
| 24B drive magnet | 25A bearing spacer |
| 26 ring bearing | 26B ring bearing |
| 27A bearing | 28 thermal couple |
| 28A thermal couple | 28B thermal couple |
| 30 outlet | 30A outlet |
| 31A bearing | 32 o-ring |
| 32B o-ring | 33A bearing |
| 34 screw | 34B screw |
| 35A magnet holder | 36 inlet |
| 36B inlet | 37A lower external retainer ring |
| 38 retainer ring | 38A internal retainer ring |
| 38B retainer ring | 40 thread |
| 40A thread | 40B thread |
| 42 coupling magnet | 42A coupling magnet |
| 42B coupling magnet | 44 bob |
| 44A bob | 44B bob |
| 46 gap | 46A gap |
| 48 bearing holder | 48A bearing holder |
| 48B bearing holder | 50 main body |
| 50A cell body | 50B cell body |
| 52 magnet holder | 52B magnet holder |
| 54 set screw | 54B set screw |
| 56 sample fluid | 56A sample fluid |
| 58A conical surface | 60A conical surface |
| 70 in-line viscometer | 70A viscometer |
| 70B in-line viscometer | |

DESCRIPTION

FIG. 1—Preferred Embodiment

FIG. 1 is a cross-section view of an in-line viscometer 70 with a main body 50 having a central area which is open at the bottom and has an inlet 36 on one side and an outlet 30 on the opposite side. A sample fluid 56 enters the interior of main body 50 via inlet 36, fills the interior of main body 50, and exits via outlet 30.

Extending up through the bottom of main body 50 is a cylindrical main shaft 22, which is attached to the bottom of main body 50 via a screw 34. An o-ring 32 is installed onto main shaft 22 to assure against leakage and a thermal couple 28 is installed into main shaft 22 to measure temperature.

The top portion of main shaft 22 has a substantially reduced outside diameter and is in contact with and can support a bob assembly 19. Bob assembly 19 comprises a bearing holder 48 with a jewel bearing 20 fitted into the top of bearing holder 48, a ring bearing 26 installed at the bottom of bearing holder 48, a retainer ring 38 supporting ring bearing 26, a bob 44 screwed onto the top of bearing holder 48 via a thread 40, and a coupling magnet 42 which is set inside bob 44. Positioning coupling magnet 42 inside bob 44 is very important. If coupling magnet 42 is allowed to have direct contact with sample fluid 56, small hematite particles could cling to coupling magnet 42 and negatively affect measurement accuracy. On the other hand, a typical sample fluid 56 tested in a standard in-line viscometer can be dirty and contain hematite particles. Positioning coupling magnet 42 inside bob 44 considerably reduces the capacity of hematite particles to cling to coupling magnet 42.

Ring bearing 26 restricts the circumferential movement of bob assembly 19. Sample fluid 56 fills a gap 46 between bob assembly 19 and main body 50. Jewel bearing 20 provides vertical support to bob assembly 19.

A pin 18 is installed inside the top of main body 50 and restricts the vertical movement of bob assembly 19. A magnet holder 52 is disposed above main body 50 and extends down around main body 50. A drive magnet 24 is installed onto the lower end of magnet holder 52 diagonally above the position of coupling magnet 42. Magnet holder 52 is connected to a motor shaft 14 via a set screw 54. Motor shaft 14 is connected to a motor 10 which is used to rotate magnet holder 52.

OPERATION

FIG. 1—Preferred Embodiment

To assemble and operate the in-line viscometer 70 shown in FIG. 1, assemble bob assembly 19 by installing ring bearing 26, retainer ring 38, and jewel bearing 20 onto bearing holder 48. Install coupling magnet 42 into bob 44 and screw bob 44 onto bearing holder 48 via thread 40. Insert thermal couple 28 into main shaft 22 for temperature measurement. Insert main shaft 22 into bob assembly 19 so that main shaft 22 contacts jewel bearing assembly 20. Install o-ring 32 onto main shaft 22 to assure against leakage.

Insert pin 18 into the top of main body 50. Install main shaft 22 and bob assembly 19 into main body 50 and attach main shaft 22 to main body 50 via screw 34. Insert motor shaft 14, which is attached to motor 10, into magnet holder 52 and secure with set screw 54. Drive magnet 24 is attached to magnet holder 52.

Motor 10 turns motor shaft 14 and causes magnet holder 52 to rotate as sample fluid 56 flows in from inlet 36, fills gap 46, and exits via outlet 30. Because of the magnetic coupling between drive magnet 24 and coupling magnet 42, as magnet holder 52 rotates, bob assembly 19 also rotates at the same speed as drive magnet 24. Drive magnet 24 is arranged diagonally above coupling magnet 42 so that drive magnet 24 not only causes bob assembly 19 to rotate, but also fully or partially suspends bob assembly 19. Because bearing friction is reduced when axial load on the bearing is reduced, this arrangement substantially reduces measurement errors due to bearing friction. Pin 18 limits excessive upward movement of bob assembly 19 and jewel bearing 20 limits excessive downward movement of bob assembly 19. This is very important in an in-line viscometer because of the wide variation of sample fluid 56 density and flow rate. When sample fluid 56 density is high, this provides higher buoyant force to bob assembly 19. When sample fluid 56 flow rate is high, this would push bob assembly 19 upward more, due to fluid flow and bob assembly 19 is located at a higher elevation relative to inlet 36 and outlet 30, as shown in FIG. 1. Thus, the current design is very robust toward flow disturbance, which is critical in an in-line viscometer. Also, the uplifting force applied on bob assembly 19 due to fluid flow will counter the force of gravity on bob assembly 19 and thus less force will be applied on jewel bearing 20, thus resulting in less friction force.

Motor 10 is a precision, low-friction motor with the capability of direct reading of its own power consumption or driving torque from its own controller.

By measuring the electrical energy or driving torque of motor 10 needed to rotate bob assembly 19, the viscosity of sample fluid 56 may be determined.

DESCRIPTION

Figure 2:
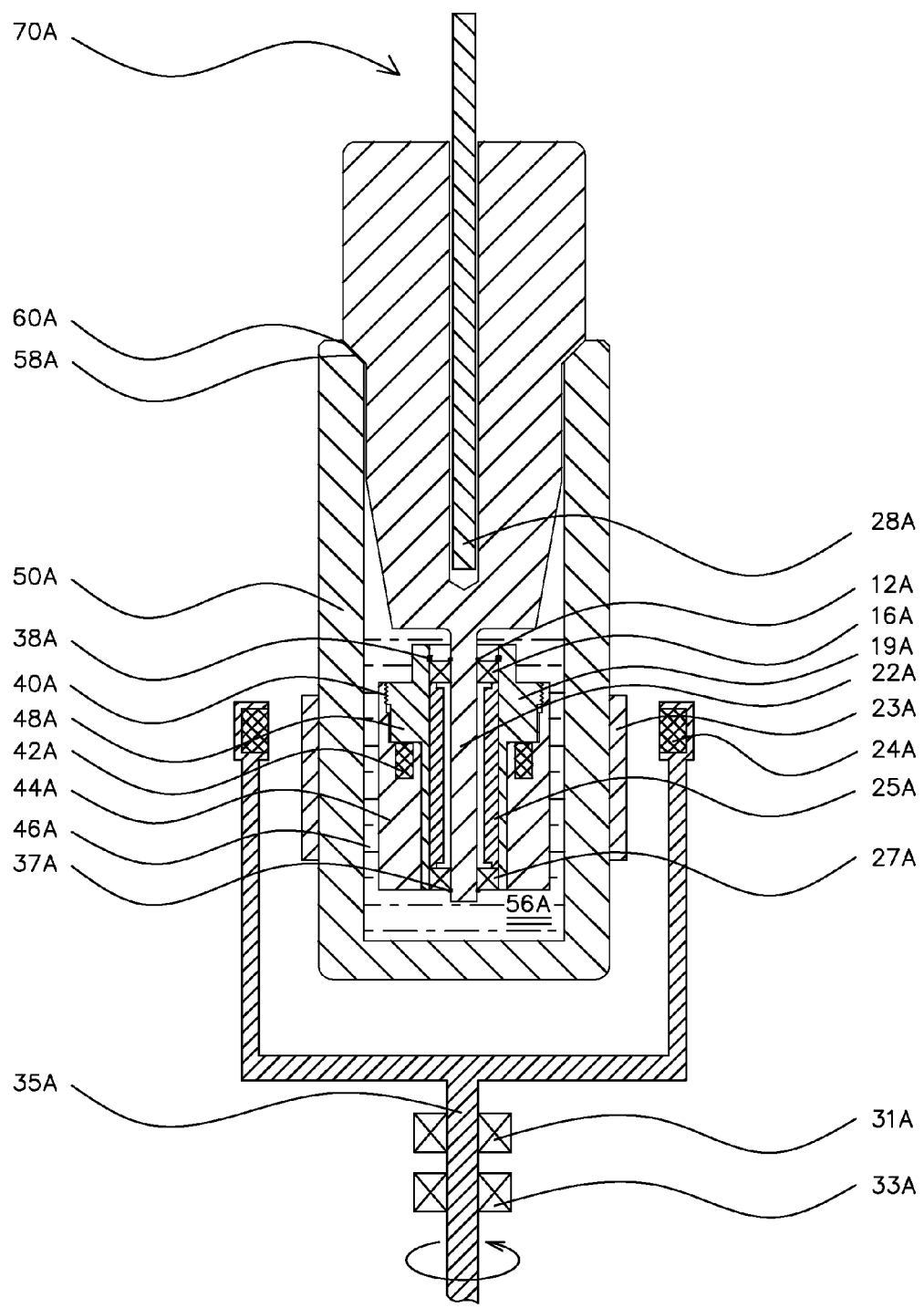
FIG. 2 is a cross-section view of a viscometer 70A in a second embodiment of the invention.

FIG. 2—Second Embodiment

FIG. 2 is a cross-section view of an in-line viscometer 70A. A magnet holder 35A is rotationally supported on the outside of a cell body 50A by a bearing 31A and a bearing 33A. Magnet holder 35A can be rotated by any conventional means such as a gear box or motor. A drive magnet 24A is mounted on magnet holder 35A.

Cell body 50A is filled with a sample fluid 56A. A bob assembly 19A is installed onto a bob holder 22A and can rotate on the same axis as bob holder 22A while being immersed in sample fluid 56A. Bob assembly 19A comprises an upper external retainer ring 12A, an internal retainer ring 38A, a bearing 16A, a bearing 27A, a bearing holder 48A, a bearing spacer 25A, a lower external retainer ring 37A, a bob 44A, and a coupling magnet 42A. Bearing holder 48A is screwed onto bob 44A via a thread 40A. Coupling magnet 42A is installed inside bob 44A diagonally below the level where drive magnet 24A is mounted on magnet holder 35A. Positioning coupling magnet 42A inside bob 44A is very important. If coupling magnet 42A is allowed to have direct contact with sample fluid 56A, small hematite particles could cling to coupling magnet 42A and negatively affect measurement accuracy. On the other hand, a typical sample fluid 56A tested in a viscometer can be dirty and contain hematite particles. Positioning coupling magnet 42A inside bob 44A considerably reduces the capacity of hematite particles to cling to coupling magnet 42A. There is a gap 46A between bob assembly 19A and a cell body 50A.

Bob holder 22A extends up to the top of cell body 50A. A conical surface 60A on bob holder 22A rests against a conical surface 58A on cell body 50A, ensuring that bob holder 22A is positioned correctly inside cell body 50A. A heater 23A heats cell body 50A while a thermal couple 28A is inserted into bob holder 22A to provide temperature feedback for temperature control.

OPERATION

FIG. 2—Second Embodiment

To assemble and operate the viscometer 70A, install coupling magnet 42A into bob 44A, then slide bob 44A onto bob holder 22A and screw bob 44A onto bearing holder 48A via thread 40A. Install internal retainer ring 38A into bearing holder 48A. Install upper external retainer ring 12A, then install bearing 16A, bearing spacer 25A, and bearing 27A onto bob holder 22A to complete bob assembly 19A. Slide bob assembly 19A onto bob holder 22A and install lower external retainer ring 37A onto bob holder 22A below bearing holder 48A. Bob assembly 19A should now be able to rotate on the same axis as bob holder 22A.

Pour sample fluid 56A into cell body 50A, then drop bob holder 22A into cell body 50A so that the bob assembly 19A is submerged in sample fluid 56A, which fills the gap 46A between bob assembly 19A and cell body 50A. Due to the design of conical surface 58A on cell body 50A and conical surface 60A on bob holder 22A, bob holder 22A is positioned in the center of cell body 50A. Insert thermal couple 28A into bob holder 22A to provide feedback for temperature control.

Magnet holder 35A is driven to rotate on bearing 31A and bearing 33A at desired speed, carrying drive magnet 24A and causing coupling magnet 42A and bob 44A to rotate as well. Drive magnet 24A is arranged diagonally above coupling magnet 42A so that drive magnet 24A not only causes bob 44A to rotate, but also at least partially suspends it on bob holder 22A. Because bearing friction is reduced when the axial load on the bearing is reduced, this arrangement substantially reduces measurement errors due to bearing friction. Upper external retainer ring 12A limits excessive upward movement of bob 44A and lower external retainer ring 37A limits excessive downward movement of bob 44A.

Heater 23A heats cell body 50A while thermal couple 28A provides temperature feedback for temperature control. By measuring the electrical energy needed to rotate bob assembly 19A, the viscosity of sample fluid 56A may be determined.

DESCRIPTION

Figure 3:
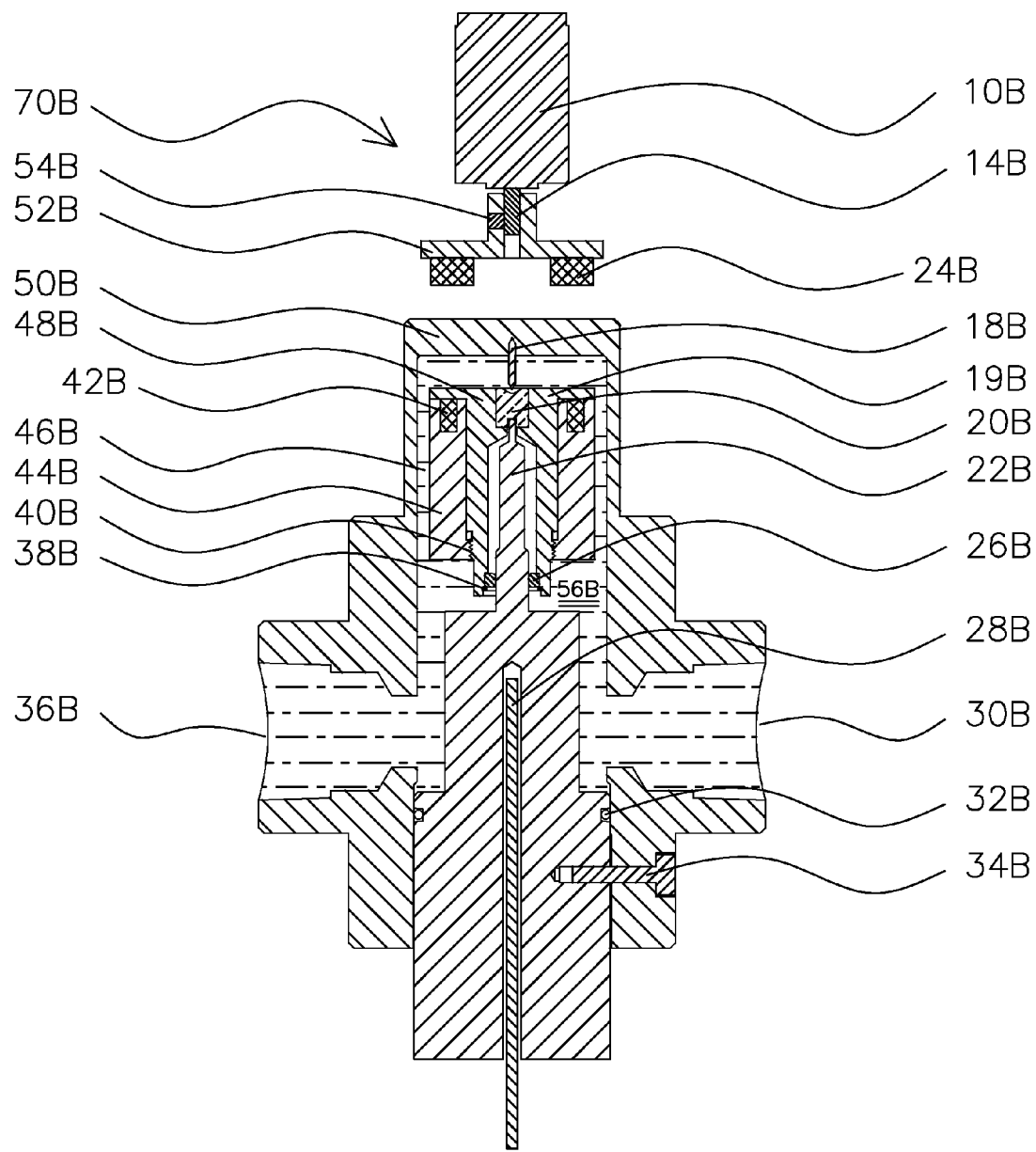
FIG. 3 is a cross-section view of an in-line viscometer 70B in a third embodiment of the invention

FIG. 3—Third Embodiment

FIG. 3 is a cross-section view of an in-line viscometer 70B with a main body 50B having a central area which is open at the bottom and has an inlet 36B on one side and an outlet 30B on the opposite side. A sample fluid 56B enters the interior of main body 50B via inlet 36B, fills the interior of main body 50B, and exits via outlet 30B.

Extending up through the bottom of main body 50B is a cylindrical main shaft 22B, which is attached to the bottom of main body 50B via a screw 34B. An o-ring 32B is installed onto main shaft 22B to assure against leakage and a thermal couple 28B is installed into main shaft 22B to measure temperature.

The top portion of main shaft 22B has a substantially reduced outside diameter and is in contact with and can support a bob assembly 19B. Bob assembly 19B comprises a bearing holder 48B with a jewel bearing 20B fitted into the top of bearing holder 48B, a ring bearing 26B installed at the bottom of bearing holder 48B, a retainer ring 38B supporting ring bearing 26B, a bob 44B screwed onto the top of bearing holder 48B via a thread 40B, and a coupling magnet 42B which is set inside bob 44B. Positioning coupling magnet 42B inside bob 44B is very important. If coupling magnet 42B is allowed to have direct contact with sample fluid 56B, small hematite particles could cling to coupling magnet 42B and negatively affect measurement accuracy. On the other hand, a typical sample fluid 56B tested in a standard in-line viscometer can be dirty and contain hematite particles. Positioning coupling magnet 42B inside bob 44B considerably reduces the capacity of hematite particles to cling to coupling magnet 42B.

Ring bearing 26B restricts the circumferential movement of bob assembly 19B. Sample fluid 56B fills a gap 46B between bob assembly 19B and main body 50B. Jewel bearing 20B provides vertical support to bob assembly 19B.

A pin 18B is installed inside the top of main body 50B and restricts the vertical movement of bob assembly 19B. A magnet holder 52B is disposed above main body 50B. A drive magnet 24B is installed onto the lower end of magnet holder 52B. Magnet holder 52B is connected to a motor shaft 14B via a set screw 54B. Motor shaft 14B is connected to a motor 10B which is used to rotate magnet holder 52B.

OPERATION

FIG. 3—Third Embodiment

To assemble and operate the in-line viscometer 70B shown in FIG. 3, assemble bob assembly 19B by installing ring bearing 26B, retainer ring 38B, and jewel bearing 20B onto bearing holder 48B. Install coupling magnet 42B into the top of bob 44B and screw bob 44B onto bearing holder 48B via thread 40B. Insert thermal couple 28B into main shaft 22B for temperature measurement. Insert main shaft 22B into bob assembly 19B so that main shaft 22B contacts jewel bearing assembly 20B. Install o-ring 32B onto main shaft 22B to assure against leakage.

Insert pin 18B into the top of main body 50B. Install main shaft 22B and bob assembly 19B into main body 50B and attach main shaft 22B to main body 50B via screw 34B. Insert motor shaft 14B, which is attached to motor 10B, into magnet holder 52B and secure with set screw 54B. Drive magnet 24B is attached to magnet holder 52B.

Motor 10B turns motor shaft 14B and causes magnet holder 52B to rotate as sample fluid 56B flows in from inlet 36B, fills gap 46B, and exits via outlet 30B. Because of the magnetic coupling between drive magnet 24B and coupling magnet 42B, as magnet holder 52B rotates, bob assembly 19B also rotates at the same speed as drive magnet 24B. Drive magnet 24B is arranged directly above coupling magnet 42B so that drive magnet 24B not only causes bob assembly 19B to rotate, but also fully or partially suspends bob assembly 19B. Because bearing friction is reduced when axial load on the bearing is reduced, this arrangement substantially reduces measurement errors due to bearing friction. Pin 18B limits excessive upward movement of bob assembly 19B and jewel bearing 20B limits excessive downward movement of bob assembly 19B. This is very important in an in-line viscometer because of the wide variation of sample fluid 56B density and flow rate. When sample fluid 56B density is high, this provides higher buoyant force to bob assembly 19B. When sample fluid 56B flow rate is high, this would push bob assembly 19B upward more, due to fluid flow and bob assembly 19B is located at a higher elevation relative to inlet 36B and outlet 30B, as shown in FIG. 3. Thus, the current design is very robust toward flow disturbance, which is critical in an in-line viscometer. Also, the uplifting force applied on bob assembly 19B due to fluid flow will counter the force of gravity on bob assembly 19B and thus less force will be applied on jewel bearing 20B, thus resulting in less friction force.

Motor 10B is a precision, low-friction motor with the capability of direct reading of its own power consumption or driving torque from its own controller.

By measuring the electrical energy or driving torque of motor 10A needed to rotate bob assembly 19B, the viscosity of sample fluid 56B may be determined.

RAMIFICATIONS

In FIG. 1, bob assembly 19 does not have to be cylindrical type; it could have vane type fins on its outside surface or could be any spindle shape.

In FIG. 1, jewel bearing 20 and ring bearing 26 can be replaced with other kinds of mechanical bearing means, as long as the bearing means can restrict the non-rotational movement of bob assembly 19.

In FIG. 1, ring bearing 26 can be replaced with roller bearings or other equivalent bearings.

In FIG. 1, in-line viscometer 70 can be turned upside down or at any angle and it will still function properly.

In FIG. 1, in-line viscometer 70 is designed to sustain a certain level of pressure. A high pressure rating can be achieved by increasing the wall thickness of main body 50.

In FIG. 1, if sample fluid 56 does not include a high content of hematite or otherwise magnetically-sensitive material, coupling magnet 42 can come into direct contact with sample fluid 56 without negatively affecting test result accuracy.

In FIG. 2, viscometer 70A can be easily modified to sustain a certain level of pressurization by adding a seal at the top of main body 50A.

In FIG. 2, bearing 16A and bearing 27A can be replaced with other kinds of mechanical bearing means, as long as the bearing means can restrict the non-rotational movement of bob assembly 19A.

In FIG. 2, if sample fluid 56A does not include a high content of hematite or otherwise magnetically-sensitive material, coupling magnet 42A can come into direct contact with sample fluid 56A without negatively affecting test result accuracy.

In FIG. 2, coupling magnet 42A could be mounted on top of bob assembly 19A instead of hidden inside of bob assembly 19A.

In FIG. 3, in-line viscometer 70B is designed to sustain a certain level of pressure. A high pressure rating can be achieved by increasing the wall thickness of main body 50B.

In FIG. 3, jewel bearing 20B and ring bearing 26B can be replaced with other kinds of mechanical bearing means, as long as the bearing means can restrict the non-rotational movement of bob assembly 19B.

In FIG. 3, in-line viscometer 70B can be turned upside down or at any angle and it will still function properly.

In FIG. 3, if sample fluid 56B does not include a high content of hematite or otherwise magnetically-sensitive material, coupling magnet 42B can come into direct contact with sample fluid 56B without negatively affecting test result accuracy.

CONCLUSION AND SCOPE

Accordingly, the reader skilled in the art will see that this invention can be used to construct an in-line test environment in which the viscosity of a fluid can be determined within the working environment of the fluid. In so doing, it satisfies an eminent need for any industry which requires the movement of viscous fluid through a pipe or manifold.

OBJECTS AND ADVANTAGES

From the description above, a number of advantages of my viscometer become evident:
a. The viscosity of a fluid can be measured within the working environment of the fluid (such as a pipe or manifold) without negatively affecting the integrity or function of the working environment.
b. Due to the limited number of components, the current invention is easy to operate and maintain.
c. Due to the principle of magnetic suspension, substantially less friction is created between the moving parts of the viscometer.

Further objects and advantages of my invention will become apparent from a consideration of the drawings and ensuing descriptions.

The invention claimed is:
1. Viscometer instrument comprising:
a) a sample fluid to be tested,
b) a container containing said sample fluid,
c) a bob within said container and immersed in said sample fluid,
d) bearing means for rotationally suspending said bob while limiting its other movements,
e) a driven magnet attached to said bob, f) a drive magnet located outside of said container coupled with said driven magnet to rotate said bob, g) a motor shaft which rotates together with said drive magnet, h) means for directly sensing the energy consumption required to rotate said motor shaft.

2. The instrument of claim 1 wherein said driven magnet is sealed inside of said bob and does not directly contact said sample.

3. The instrument of claim 1 wherein said drive magnet is located above the level of the driven magnet to provide upward lifting force on said driven magnet and bob as well.

4. The instrument of claim 1 wherein said bob has cylindrical shape.

5. The instrument of claim 1 wherein said bob has fins on its outside surface.

6. The instrument of claim 1 wherein said bearing means consists of an end bearing limiting the vertical movement of said bob and a roller or ring bearing limiting radial movement of said bob.

7. The instrument of claim 1 wherein said bearing means consists of two roller or ring bearing limiting radial and vertical movement of said bob.

8. An in-line viscometer instrument comprising:

a) a sample fluid to be tested, b) a container containing said sample fluid, c) an inlet and an outlet on said container for said sample fluid, d) a bob within said container and immersed in said sample fluid, e) bearing means for rotationally suspending said bob while limiting its other movements, f) a driven magnet attached to said bob and immersed in said sample fluid as well, g) a drive magnet located outside of said container coupled with said driven magnet to rotate said bob, h) a motor shaft which rotates together with said drive magnet, i) means for sensing the energy consumption required to rotate said motor shaft.

9. The instrument of claim 8 wherein said bob is positioned at a higher elevation compared to said inlet and said outlet on said container.

10. The instrument of claim 8 wherein said driven magnet is sealed inside of said bob and does not directly contact said sample.

11. The instrument of claim 8 wherein said drive magnet is located above the level of driven magnet to provide upward lifting force on said driven magnet and bob as well.

12. The instrument of claim 8 wherein said bob has cylindrical shape.

13. The instrument of claim 8 wherein said bearing means consists of an end bearing limiting the vertical movement of said bob and a roller or ring bearing limiting radial movement of said bob.

14. The instrument of claim 8 wherein said bearing means consists of two roller or ring bearing limiting radial and vertical movement of said bob.

15. An in-line viscometer instrument comprising:

a) a sample fluid to be tested, b) an open-top container containing said sample fluid c) a bob within said container and immersed in said sample fluid, d) bearing means for rotationally suspending said bob while limiting its other movements, e) a driven magnet attached to said bob and immersed in said sample fluid, f) a drive magnet located outside of said container coupled with said driven magnet to rotate said bob, g) a motor shaft which rotates together with said drive magnet, h) means for sensing the energy consumption required to rotate said motor shaft.

16. The instrument of claim 15 wherein said driven magnet is sealed inside of said bob and does not directly contact said sample.

17. The instrument of claim 15 wherein said drive magnet is located above the level of the driven magnet to provide upward lifting force on said driven magnet and bob as well.

18. The instrument of claim 15 wherein said bob has cylindrical shape.

19. The instrument of claim 15 wherein said bearing means consists of an end bearing limiting the vertical movement of said bob and a roller or ring bearing limiting radial movement of said bob.

20. The instrument of claim 15 wherein said bearing means consists of two roller or ring bearings limiting radial and vertical movement of said bob.

* * * * *